United States Patent
Blaauw et al.

(10) Patent No.: US 6,759,556 B2
(45) Date of Patent: Jul. 6, 2004

(54) PROCESS FOR THE PRODUCTION OF CYCLOHEXANONE OXIME

(75) Inventors: Marc Blaauw, Maastricht (NL); Theodorus Friederich Maria Riesthuis, Obbicht (NL); Alex Pit, Georgia, GA (US); Henk Oevering, Elsloo (NL); Antonius Jacobus Franciscus Simons, Geleen (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/297,181

(22) PCT Filed: May 31, 2001

(86) PCT No.: PCT/NL01/00428
§ 371 (c)(1),
(2), (4) Date: Aug. 28, 2003

(87) PCT Pub. No.: WO01/94297
PCT Pub. Date: Dec. 13, 2001

(65) Prior Publication Data
US 2004/0039231 A1 Feb. 26, 2004

(30) Foreign Application Priority Data
Jun. 5, 2000 (EP) .......................................... 00201970

(51) Int. Cl.$^7$ ............................................. C07C 249/08
(52) U.S. Cl. ...................................................... 564/267
(58) Field of Search ....................................... 567/267

(56) References Cited

U.S. PATENT DOCUMENTS 3,720,755 A    3/1973    Duyverman et al.

FOREIGN PATENT DOCUMENTS

GB    1284515    8/1972

*Primary Examiner*—Taofiq Solola
(74) *Attorney, Agent, or Firm*—Pillsbury Winthrop LLP

(57) ABSTRACT

Process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone to form cyclohexanone oxime, wherein the phosphate concentration in the acqueous reaction medium entering the cyclohexanone oxime synthesis zone is higher than 3.0 mol/l.

12 Claims, 1 Drawing Sheet

PROCESS FOR THE PRODUCTION OF CYCLOHEXANONE OXIME

CROSS REFERENCE TO RELATED APPLICATIONS

This application is the National Phase of International Application PCT/NL01/00428 filed May 31, 2001 which designated the U.S., and which further claims priority to European application No. 00201970.1, filed Jun. 5, 2000, both of which are hereby incorporated in their entirety by reference.

The invention relates to a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone in the presence of an organic solvent to form cyclohexanone oxime.

Oximes can be produced in a process in which a buffered, aqueous reaction medium containing buffer acids or acidic salts, for example phosphate buffers, and buffer salts derived from these acids, is continuously recycled between a hydroxylammonium synthesis zone, in which nitrate ions are catalytically reduced with molecular hydrogen to hydroxylammonium, and an oxidation zone where a ketone, e.g. cyclohexanone, is converted to an oxime. Before the aqueous reaction medium is passed into the hydroxylammonium synthesis zone, it may be enriched with the required nitrate ions by addition of nitric acid or by absorption of nitrous gases in the aqueous reaction medium in which instance nitric acid is formed in situ. After having been enriched in hydroxylammonium in the hydroxylammonium synthesis zone, the aqueous reaction medium is then passed to the oxime synthesis zone, where the hydroxylammonium reacts with a ketone,e.g., cyclohexanone, forming the corresponding oxime. The oxime can then be separated from the aqueous reaction medium which is recycled to the hydroxylammonium synthesis zone.

The net chemical reactions occurring during the process can be represented by the following equations.
1) Preparation of the hydroxylammonium:

$$2H_3PO_4+NO_3^-+3H_2 \rightarrow NH_3OH^++2H_2PO_4^-+2H_2O$$

2) Preparation of the oxime

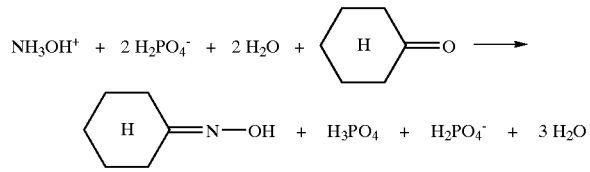

3) Supply of $HNO_3$ to make up the depletion of the source of nitrate ions after removal of the oxime formed

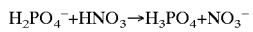
$$H_2PO_4^-+HNO_3 \rightarrow H_3PO_4+NO_3^-$$

The catalyst used in the reduction of the nitrate ions is generally palladium and/or platinum on a carrier material of carbon or alumina, the carrier material being loaded with from 1 to 25% wt. of palladium and/or platinum. The activity of the catalyst is adversely affected by the presence of organic contaminants, such as the ketone and oxime, in the recycled stream.

A number of techniques have been developed to address this problem of the recycled stream containing high amounts of contaminants that poison the catalyst U.S. Pat. No. 3,940,442 describes that poisoning of the catalyst is prevented by heating the aqueous reaction medium being recycled from the cyclohexanone oxime synthesis zone to the hydroxylammonium synthesis zone to an elevated temperature in the range of 50° C. to 106° C. GB-A-1,283,894 and U.S. Pat. No. 3,997,607 describe that heat treating the aqueous reaction medium in the presence of nitrous acid, respectively nitrous gases reduce the extent of catalyst poisoning.

It has now been found that an increased phosphate concentration in the aqueous reaction medium entering the cyclohexanone oxime synthesis zone results in a decrease of the concentration of the organic contaminants in the aqueous reaction medium which is recycled from the cyclohexanone oxime synthesis zone to the hydroxylammonium synthesis zone.

Therefore, the invention provides a process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone in the presence of an organic solvent to form cyclohexanone oxime, characterized in that the phosphate concentration in the aqueous reaction medium entering the cyclohexanone oxime synthesis zone is higher than 3.0 mol/l. The invention also provides a process for the production of cyclohexanone oxime in which an aqueous reaction medium containing hydroxylammonium, phosphate and nitrate is fed into a cyclohexanone oxime synthesis zone, in which hydroxylammonium is reacted in the presence of an organic solvent with cyclohexanone to form cyclohexanone oxime, characterized in that the phosphate concentration in the aqueous reaction medium entering the cyclohexanone oxime synthesis zone is higher than 3.0 mol/l.

Using the process according to the invention it is possible to decrease the amount of organic contaminants which poison the catalyst, in particular residual cyclohexanone and/or cyclohexanone oxime, entering the hydroxylammonium synthesis zone under further equal circumstances. According to the invention it is also possible to omit steps for the removal of organic contaminants or to lessen the extent to which such steps are carried out, for instance by using smaller equipment, the increased phosphate concentration avoiding or mitigating an increase of the amount of organic contaminants entering the hydroxylammonium synthesis zone. According to the invention, it is also possible to increase the concentration hydroxylammonium in the aqueous reaction medium entering the cyclohexanone oxime systhesis zone, the increased phosphate concentration avoiding or mitigating an increase of the amount of organic contaminants entering the hydroxylammonium synthesis zone.

According to the invention, the phosphate concentration in the aqueous reaction medium entering the cyclohexanone oxime synthesis zone is higher than 3.0 mol/l. As used herein, the phosphate concentration denotes the sum concentration of all phosphates, irrespective of the form in which they are present, expressed in mol per liter of aqueous reaction reaction medium. Preferably, the phosphates are present as $PO_4^{3-}$, $HPO_4^{2-}$, $H_2PO_4^-$, $H_3PO_4$, salts of $PO_4^{3-}$, $HPO_4^{2-}$, $H_2PO_4^-$, and/or combinations thereof.

Preferably, the phosphate concentration in the aqueous reaction medium entering the cyclohexanone oxime synthesis zone is higher than 3.3 mol/l, more preferably higher than 3.4 mol/l, in particular higher than 3.5 mol/l, more in particular higher than 3.7 mol/l. Increasing the phosphate concentration results in a further decrease of the concentration of the organic contaminants exiting th cyclohexanone oxime synthesis zone. There is no specific upper limit for the phosphate centration. Preferably, the phosphate concentration is chosen such that no crystallization occurs, which depends, inter alia, on the temperature and the concentration of other components in the aqueous reaction medium. Generally, the phosphate concentration in the aqueous reaction medium entering the cyclohexanone oxime synthesis zone is lower than 8 mol/l, preferably lower than 5 mol/l, more preferably lower than 4.5 mol/l.

There is no specific lower limit for the concentration hydroxylammonium in the aqueous reaction medium entering the cyclohexanone oxime synthesis zone. Preferably, the concentration hydroxylammonium in the aqueous reaction medium entering the cyclohexanone oxime synthesis zone is higher than 0.8 mol/l. An increased concentration of hydroxylammonium is advantageous, since the conversion of hydroxylammonium in the cyclohexanone oxime synthesis zone may then be increased. Furthermore, the amount of cyclohexanone oxime produced per unit of time can be increased by increasing the concentration hydroxylammonium in the aqueous reaction medium entering the cyclohexanone oxime synthesis zone. Preferably, the concentration hydroxylammonium in the aqueous reaction medium entering the cyclohexanone oxime synthesis zone is higher than 1.0 mol/l, more preferably higher than 1.1. mol/l, in particular higher than 1.2 mol/l, more in particular higher than 1.4 mol/l, most preferably higher than 1.6 mol/l. An increased concentration hydroxylammonium in the aqueous reaction medium entering the cyclohexanone oxime synthesis zone may for instance be achieved by increasing the residence time in the hydroxylammonium synthesis zone and/or by increasing the nitrate concentration in the aqueous reaction medium entering the hydroxylammonium synthesis zone. There is no specific upper limit for the concentration hydroxylammonium in the aqueous reaction medium entering the cyclohexanone oxime synthesis zone. Generally, the concentration hydroxylammonium in the aqueous reaction medium entering the cyclohexanone oxime synthesis zone is below 2.5 mol/l.

We have found that an increase of the concentration hydroxylammonium in the aqueous reaction medium entering the cyclohexanone oxime systhesis zone may result in an increase of the concentration of organic contaminants in the aqueous reaction medium exiting the cyclohexanone oxime synthesis zone. The process according to th invention has the advantage that this effect is mitigated or avoided.

Preferably, in the aqueous reaction medium entering the cyclohexanone oxime synthesis zone, the ratio c(phosphate)/c($NH_3OH^+$) is higher than 2.0, more preferably higher than 2.1, in particular higher than 2.2, more in particular higher than 2.3, most preferably higher than 2.4, wherein c(phosphate) represents the phosphate concentration (in mol/l) and c($NH_3OH^+$) represents the concentration hydroxylammonium (in mol/l). An increased ratio is advantageous, since it results in a decrease of the amount of organic contaminants entering the hydroxylammonium synthesis zone under further equal circumstances. There is no specific upper limit for the ratio. If the ratio is too high, the process may become less attractive from an economical point of view. In general, the ratio c(phosphate)/c($NH_3OH^+$) is less than 10.

In the cyclohexanone oxime synthesis zone, hydroxylammonium is reacted with cyclohexanone to form cyclohexanone oxime. Preferably, the aqueous reaction medium and the cyclohexanone are contacted in countercurrent flow. It is preferred that cyclohexanone, the organic solvent and the aqueous reaction medium are contacted in the cyclohexanone oxime synthesis zone and that an organic medium comprising the organic solvent and cyclohexanone oxime is withdrawn from the cyclohexanone oxime synthesis zone. This is a very effective way of separating cyclohexanone oxime from the aqueous reaction medium. A suitable process in which an organic solvent is used is for instance described in GBA-A-1,138,750. Most preferably, the aqueous reaction medium and a stream comprising the cyclohexanone and the organic solvent are contacted in countercurrent flow. Use may be made of known types of counterflow reactors, such as for instance pulsed columns filled with packing bodies or rotating disc reactors. It is also possible to use a system comprising a number, e.g. 3 to 6, of series-connected reactors equipped with stirrers, each of these reactors also being provided with a liquid-liquid separator. Any organic solvent may be used in which cyclohexanone and cyclohexanone oxime may be dissolved, such as for instance alcohols, ketones, esters, ethers, hydrocarbons, and mixtures of the same. Preferably, the organic solvent has a solubility in water of less than 0.1% by weight at 20° C. Preferably, the organic solvent is selected from the group consisting of benzene, toluene, xylene, methylcyclopentane, cyclohexane and mixtures thereof. Most preferably, the organic solvent is toluene. Preferably, the cyclohexanone is dissolved in the organic solvent.

There is no specific lower limit for the concentration cyclohexanone oxime in the organic medium exiting the cyclohexanone oxime synthesis zone. Generally, the cyclohexanone oxime concentration in the organic medium exiting the cyclohexanone oxime synthesis zone is higher than 5 wt. %. An increased cyclohexanone oxime concentration in the organic medium exiting the cyclohexanone oxime synthesis zone has the advantage that separation of the organic solvent from the cyclohexanone oxime, for instance in a distillation process, can be carried out using less energy. Preferably, the cyclohexanone oxime concentration in the organic medium exiting the oxime synthesis zone is higher than 25 wt. %, more preferably higher than 30 wt. %, in particular higher than 35 wt. %, more in particular higher than 38 wt. %. An increased concentration cyclohexanone oxime may for instance be achieved by reducing the flow rate of the solvent into the oxime synthesis zone relative to the flow rate of the cyclohexanone into the oxime synthesis zone. Generally, the cyclohexanone oxime concentration in the organic medium exiting the cyclohexanone oxime synthesis zone, is lower than 95 wt. %, preferably lower than 80 wt. %, more preferably lower than 60 wt. %. All cyclohexanone oxime concentrations in the organic medium are given relative to the sum weight of the cyclohexanone oxime plus organic solvent.

We have found that an increase of the concentration cyclohexanone oxime in the organic medium exiting the cyclohexanone oxime synthesis zone may result in an increase of the concentration of organic contaminants in the aqueous reaction medium exiting the hydroxylammonium synthesis zone. The process according to the invention has the advantage that this effect is mitigated or avoided.

The cyclohexanone oxime synthesis zone may be operated at a temperature ranging from 40 to 150° C. and at atmospheric, subatmospheric, or elevated pressures, preferably between 0.05 and 0.5 MPa, more preferably between 0.1 and 0.2 MPa, most preferably between 0.1 and 0.15 MPa. Preferably, the aqueous reaction medium entering the cyclohexanone oxime synthesis zone has a pH of between 1 and 6, more preferably between 1.5 and 4.

Preferably, the aqueous reaction medium exiting the cyclohexanone oxime synthesis zone is subjected to one or more separation steps prior to entering the hydroxylammonium synthesis zone in order to reduce the amount of residual organic contaminants, in particular cyclohexanone and cyclohexanone oxime. Preferably, the aqueous reaction medium exiting the cyclohexanone oxime synthesis zone is contacted with an organic solvent in an extraction zone. The organic solvent used in the extraction zone is preferably the same as the organic solvent used in the cyclohexanone oxime synthesis zone. Any organic solvent may be used in which cyclohexanone and cyclohexanone oxime may be dissolved, such as for instance alcohols, ketones, esters, ethers, hydrocarbons, and mixtures of the same. Preferably, the organic solvent has a solubility in water of less than 0.1% by weight at 20° C. Preferably, the organic solvent is selected from the group consisting of benzene, toluene, xylene, methylcyclopentane, cyclohexane and mixtures thereof. Most preferably, the organic solvent is toluene. Use may be made of known types of extractors such as for instance an extraction column, or one or more reactors equipped with stirrers, optionally series-connected, each of these reactors also being provided with a liquid-liquid separator. Preferably, a pulsed column filled with packing bodies is used. The extraction zone is preferably operated at a temperature range from 40 to 150° C. and at atmospheric, subatmospheric, or elevated pressures, preferably between 0.05 and 0.5 MPa, more preferably between 0.1 and 0.2 MPa, most preferably between 0.1 and 0.15 MPa. Preferably, the joint content of the cyclohexanone and cyclohexanone oxime in the aqueous reaction medium exiting the extraction zone is below 0.2 wt. % (2000 ppm), more preferably below 0.05 wt. %, in particular below 0.02 wt. %, more in particular below 0.01 wt. %, most preferably below 0.005 wt. % (relative to the weight of the aqueous reaction medium).

Preferably, the aqueous reaction medium exiting the cyclohexanone oxime synthesis zone or exiting the extraction zone is subjected to stripping to achieve further reduction in organic contaminants. The stripping process described in U.S. Pat. No. 3,940,442 may for instance be used. It is preferred that the joint content of cyclohexanone and cyclohexanone in the aqueous reaction medium entering the hydroxylammonium synthesis zone is not more than 0.02 wt. % (200 ppm), more preferably not more than 0.005 wt. %, in particular not more than 0.002 wt. %, more in particular not more than 0.001 wt. % and most preferably not more than 0.0002 wt. %. (relative to the weight of the aqueous reaction medium).

Generally, the aqueous reaction medium is an acidic, buffered reaction medium. Th aqueous reaction medium may contain ammonium ($NH_4^+$), for instance formed as a by-product in the synthesis of hydroxylammonium. Preferably, in the aqueous reaction medium entering the cyclohexanone oxime synthesis zone, the ratio $c(NH_4^+)/c$(phosphate) is bin 0.1 and 3, more preferably between 0.2 and 2, most preferably between 0.5 and 1.5, wherein $c(NH_4^+)$ represents the concentration of $NH_4^+$ in mol/l and c(phosphate) represents the phosphate concentration in mol/l.

Generally, the aqueous reaction medium entering the cyclohexanone oxime synthesis zone contains nitrate ($NO_3^-$). Preferably, in the aqueous reaction medium entering the cyclohexanone oxime synthesis zone, the $c(NO_3^-)/c$(phosphate) is between 0.05 and 1, more preferably between 0.1 and 0.5, wherein $c(NO_3^-)$ represents the concentration of $NO_3^-$ in mol/l and c(phosphate) represents the phosphate concentration in mol/l.

In the hydroxylammonium synthesis zone hydroxylammonium is formed by catalytic reduction of nitrate with hydrogen. The hydroxylammonium synthesis zone may be operated at a temperature ranging from 20 to 100° C., preferably 30–90° C., more preferably 40–65° C., and at atmospheric, subatmospheric or elevated pressures, preferably between 0.1 and 5 MPa, more preferably between 0.3 and 3 MPa, and in particular between 0.5 and 2 MPa (hydrogen partial pressure). Preferably, the pH in the hydroxylammonium synthesis zone is between 0.5 and 6, more preferably between 1 and 4. The catalyst employed in this zone is generally present in a range of between 1 to 25 wt. %, preferably between 5 to 15 wt. % of a precious metal, relative to total weight of support plus catalyst. Preferably, the catalyst is a palladium containing catalyst, for instance a palladium or a palladium-platinum catalyst, present on a support, such as for instance carbon or alumina support. Generally, the catalyst is present in the hydroxylammonium synthesis zone in an amount of 0.2–5 wt. % relative to the total liquid weight in the hydroxylammonium reactor vessel(s).

DESCRIPTION OF AN EMBODIMENT

Figure 1:
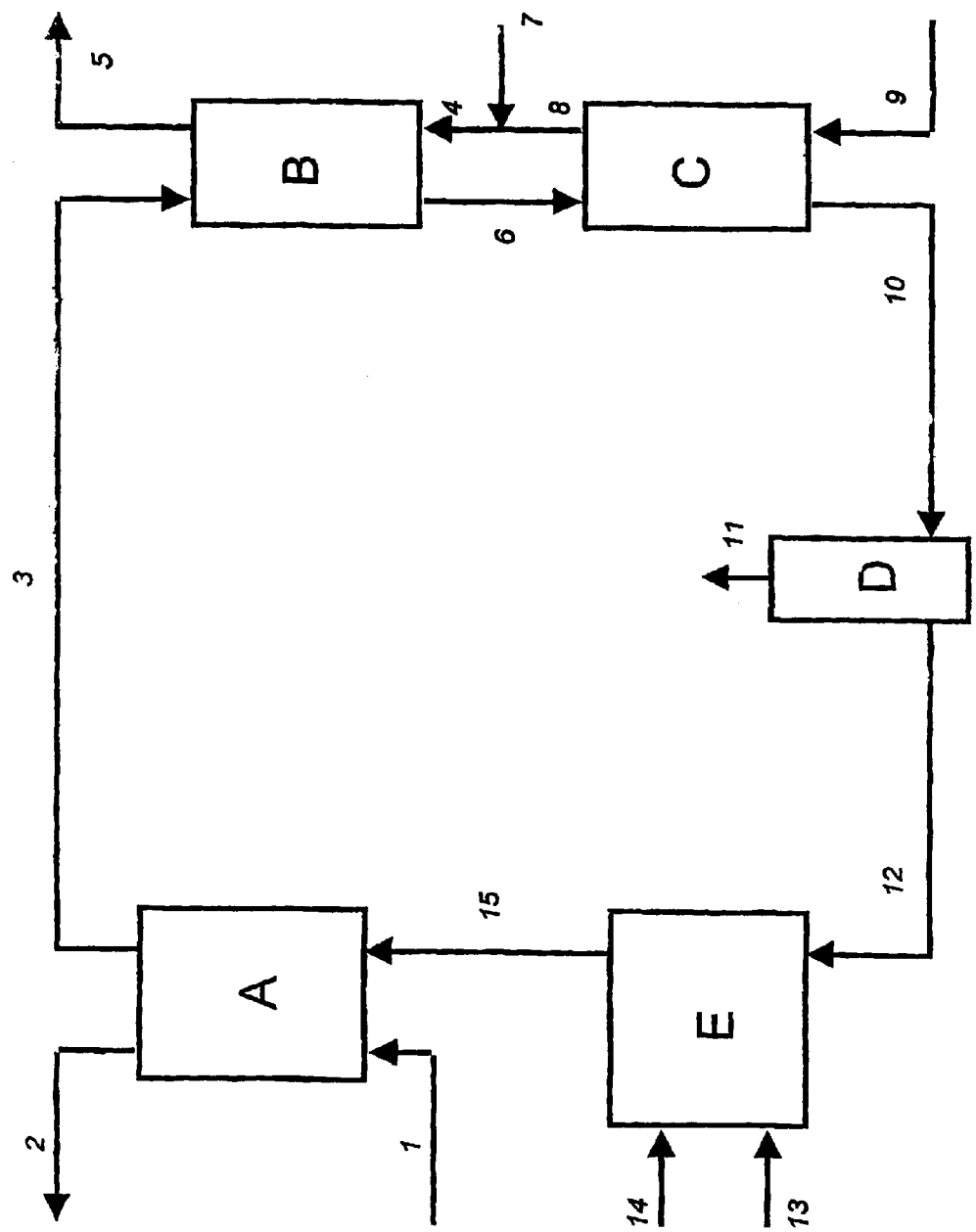
FIG. 1 is a schematic diagram of an embodiment of the process according to the present invention.

Referring to FIG. 1, A and B represent the hydroxylammonium synthesis zone and the cyclohexanone oxime synthesis zone, respectively. To zone A, containing catalyst, hydrogen is fed via line 1; unreacted hydrogen is discharged, with any other gases, via line 2. The aqueous reaction medium, containing, inter alia, phosphate, is fed to zone A through line 15 and after having been enriched in hydroxylammonium (also ammonium as a by-product) in the hydroxylammonium synthesis zone, is passed to the cyclohexanone oxime synthesis zone B via line 3. The phosphate concentration in the aqueous reaction medium which is passed from hydroxylammonium synthesis zone A to cyclohexanone oxime synthesis zone B is higher than 3.0 mol/l. The cyclohexanone to be converted is fed in an organic solvent to the oxime synthesis zone B via line 4. The cyclohexanone is introduced into the organic solvent via line 7. The largest part of cyclohexanone oxime produced and dissolved in the organic solvent is removed from the system via line 5.

Upon exiting oxime synthesis zone B, the aqueous reaction medium is passed to extraction zone C via line 6. Upon exiting oxime synthesis zone B, the hydroxylammonium content of the aqueous reaction medium has been reduced by reaction and contains small quantities of cyclohexanone and cyclohexanone oxime contaminants. The organic solvent enters extraction zone C through line 9. Within extraction zone C, additional cyclohexanone oxime is removed from the aqueous reaction medium and carried out of zone C in the organic solvent through line 8. In the extraction zone C, the residual organic contaminants (cyclohexanone+cyclohexanone oxime) in the aqeuous reaction medium is reduced.

The aqueous reaction medium exits extraction zone C through line 10 which passes the aqueous reaction medium to a separation operation, stripping column D. In this column, cyclohexanone oxime is hydrolyzed to cyclohexanone and the cyclohexanone thus formed together with the cyclohexanone already present is discharged with other organic materials and water (e.g., as an azeotrope) through line 11. The aqueous reaction medium being recycled in the system then passes through line 12 to zone E. In zone E, nitric acid is produced. Preferably, nitric acid is produced, at zone E or thereafter, by reacting air fed through line 13 with ammonia fed through line 14 and with water from the aqueous reaction medium. Directly supplying nitric acid to the aqueous reaction medium instead of producing nitric acid is also possible. Accordingly, the nitrate level is increased in the inorganic medium in zone E. In zone E, ammonium ions, e.g. formed as a by-product in the synthesis of hydroxylammonium, may be converted by means of gases containing nitrogen oxides. However, other methods for removal of ammonium ions may also be used. The aqueous reaction medium then completes the cycle by returning to hydroxylammonium synthesis zone A via line 15. The process is carried out continuously.

The following specific examples are to be construed as merely illustrative, and not limitive, of the remainder of the disclosure.

EXAMPLES 1–7

In all examples the embodiment as illustrated in FIG. 1 was used.

Example 1

In hydroxylammonium synthesis zone A (containing a catalyst (8 wt. % Pd and 2 wt. % Pt supported on carbon), operated at a temperature of 55° C. at a pressure of 1 MPa (hydrogen partial pressure)) an aqueous reaction medium having the following composition
1.30 mol $NH_3OH \cdot H_2PO_4$
1.38 mol $NH_4H_2PO_4$
0.365 mol $H_3PO_4$
1.73 mol $NH_4NO_3$
41.5 mol $H_2O$
was produced per unit of time, and continuously fed to cyclohexanone oxime synthesis zone B (a pulsed packed column, operated at 55° C.), together with cyclohexanone and toluene. The molar ratio of hydroxylammonium fed to the cyclohexanone oxime synthesis zone per unit of time to cyclohexanone fed to the cyclohexanone oxime synthesis zone per unit of time, i.e. the ratio hydroxylammonium (in mol/s)/cyclohexanone (in mol/s) was 0.95. Substantially all hydroxyl ammonium was reacted to form cyclohexanone oxime. Cyclohexanone oxime dissolved in toluene was withdrawn from the hydroxylammonium syntheses zone, the cyclohexanone concentration being 38 wt. % (relative to the sum weight of toluene+cyclohexanone oxime). The aqueous reaction medium exiting zone B was fed to extraction zone C (a pulsed packed column, operated at 70° C.), together with toluene.

The aqueous reaction medium exiting extraction zone C contained 123 ppm (0.0123 wt. %) organic residuals (cyclohexanone+cyclohexanone oxime).

Example 2

In this example all conditions are the same as in example 1, except that the aqueous reaction medium exiting hydroxylammonium synthesis zone A and entering cyclohexanone oxime synthesis zone B had the following composition
1.30 mol $NH_3OH \cdot H_2PO_4$
1.38 mol $NH_4H_2PO_4$
0.685 mol $H_3PO_4$
1.73 mol $NH_4NO_3$
39.9 mol $H_2O$
The aqueous reaction medium exiting extraction zone C contained 43 ppm organic residuals (cyclohexanone+cyclohexanone oxime).

Example 3

In this example all conditions are the same as in the previous examples, except that the aqueous reaction medium exiting hydroxylammonium synthesis zone A and entering cyclohexanone oxime synthesis zone B had the following composition
1.50 mol $NH_3OH \cdot H_2PO_4$
1.45 mol $NH_4H_2PO_4$
0.39 mol $H_3PO_4$
1.65 mol $NH_4NO_3$
39.8 mol $H_2O$
The aqueous reaction medium exiting extraction zone C contained 218 ppm organic residuals (cyclohexanone+cyclohexanone oxime).

Example 4

In this example all conditions are the same as in the previous examples, except that the aqueous reaction medium exiting hydroxylammonium synthesis zone A and entering cyclohexanone oxime synthesis zone B had the following composition
1.5 mol $NH_3OH \cdot H_2PO_4$
1.45 mol $NH_4H_2PO_4$
0.60 mol $H_3PO_4$
1.65 mol $NH_4NO_3$
37.6 mol $H_2O$
The aqueous reaction medium exiting extraction zone C contained 42 ppm organic residuals (cyclohexanone+cyclohexanone oxime).

Example 5

In this example all conditions are the same as in the previous examples, except that the aqueous reaction medium exiting hydroxylammonium synthesis zone A and entering cyclohexanone oxime synthesis zone B had the following composition
1.50 mol $NH_3OH \cdot H_2PO_4$
1.45 mol $NH_4H_2PO_4$
0.93 mol $H_3PO_4$
1.65 mol $NH_4NO_3$
36.9 mol $H_2O$
The aqueous reaction medium exiting extraction zone C contained 24 ppm organic residuals (cyclohexanone+cyclohexanone oxime).

Example 6

In this example all conditions are the same as in the previous examples, except that the aqueous reaction medium exiting hydroxylammonium synthesis zone A and entering cyclohexanone oxime synthesis zone B had the following composition
1.60 mol $NH_3OH \cdot H_2PO_4$
1.45 mol $NH_4H_2PO_4$
0.30 mol $H_3PO_4$ 1.65 mol $NH_4NO_3$
39.6 mol $H_2O$ The aqueous reaction medium exiting extraction zone C contained 277 ppm organic residuals (cyclohexanone+cyclohexanone oxime).

Example 7

In this example all conditions are the same as in the previous examples, except that the aqueous reaction medium exiting hydroxylammonium synthesis zone A and entering cyclohexanone oxime synthesis zone B had the following composition 1.6 mol $NH_3OH \cdot H_2PO_4$
1.45 mol $NH_4H_2PO_4$
0.88 mol $H_3PO_4$
1.65 mol $NH_4NO_3$
36.4 mol $H_2O$ The aqueous reaction medium exiting extraction zone C contained 26 ppm organic residuals (cyclohexanone+cyclohexanone oxime).

An overview of the examples 1 to 7 is given in the table, giving the concentration hydroxylammonium in the aqueous reaction medium entering the cyclohexanone oxime synthesis zone (in mol/l for aqueous reaction medium having a density of 1.25 mol/l), the concentration phosphate in the aqueous reaction medium entering the cyclohexanone oxime synthesis zone (in mol/l), and the concentration organic residuals (cyclohexanone oxime+cyclohexanone) in the aqueous reaction medium exiting the extraction zone.

The examples show that an increased phosphate concentration results in a decreased concentration organic residuals under further equal circumstances (e.g. constant concentration hydroxylammonium). The examples further show that an increase of the concentration organic residuals as a result of an increased concentration hydroxylammonium is avoided or mitigated by increasing the phosphate concentration.

TABLE overview of results of examples 1 to 7

| Example | Concentration hydroxylammonium (mol/l) | Phospate concentration (mol/l) | Concentration organic residuals (ppm) |
|---|---|---|---|
| 1 | 1.3 | 3.04 | 123 |
| 2 | 1.3 | 3.34 | 43 |
| 3 | 1.5 | 3.34 | 218 |
| 4 | 1.5 | 3.75 | 42 |
| 5 | 1.5 | 3.88 | 24 |
| 6 | 1.6 | 3.35 | 277 |
| 7 | 1.6 | 3.93 | 26 |

Particular embodiments of this invention have been illustrated and described above. However, those of ordinary skill in the art understand that various modifications can be made, without departing from the spirit and scope of the invention. Accordingly, interpretation of this invention should not be limited, except as by the appended claims.

What is claimed is:

1. Process for the production of cyclohexanone oxime in which a phosphate-containing aqueous reaction medium is cycled from a hydroxylammonium synthesis zone to a cyclohexanone oxime synthesis zone and back to the hydroxylammonium synthesis zone, in which hydroxylammonium synthesis zone hydroxylammonium is formed by catalytic reduction of nitrate with hydrogen, and in which cyclohexanone oxime synthesis zone hydroxylammonium is reacted with cyclohexanone in the presence of an organic solvent to form cyclohexanone oxime, characterized in that the phosphate concentration in the aqueous reaction medium entering the cyclohexanone oxime synthesis zone is higher than 3.0 mol/l.

2. Process for the production of cyclohexanone oxime in which an aqueous reaction medium containing hydroxylammonium, phosphate and nitrate is fed into a cyclohexanone oxime synthesis zone, in which hydroxylammonium is reacted with cyclohexanone in the presence of an organic solvent to form cyclohexanone oxime, characterized in that the phosphate concentration in the aqueous reaction medium entering the cyclohexanone oxime synthesis zone is higher than 3.0 mol/l.

3. Process according to claim 1 or claim 2, characterized in that the phosphate concentration in the aqueous reaction medium entering the cyclohexanone oxime synthesis zone is higher than 3.3 mol/l, preferably higher than 3.5 mol/l, more preferably higher than 3.7 mol/l.

4. Process according to any one of claim 1, characterized in that the concentration hydroxylammonium in the aqueous reaction medium entering the cyclohexanone oxime synthesis zone is higher than 0.8 mol/l.

5. Process according to claim 4, characterized in that the concentration hydroxylammonium in the aqueous reaction medium entering the oxime synthesis zone is higher than 1.0 mol/l.

6. Process according to claim 5, characterized in that the concentration hydroxylammonium in the aqueous reaction medium entering the oxime synthesis zone is higher than 1.2 mol/l, preferably higher than 1.4 mol/l, more preferably higher than 1.6 mol/l.

7. Process according to any one of claim 1, characterized in that in the aqueous reaction medium entering the cyclohexanone oxime synthesis zone, the ratio c(phosphate)/c($NH_3OH^+$)>2.0, wherein c(phosphate) represents the phosphate concentration (in mol/l) and c($NH_3OH^+$) represents the concentration hydroxylammonium (in mol/l).

8. Process according to claim 7, characterized in that in the aqueous reaction medium entering the oxime synthesis zone the ratio c(phosphate)/c($NH_3OH^+$)>2.1.

9. Process according to any one of claim 1, characterized in that cyclohexanone, the organic solvent and the aqueous reaction medium are contacted in the cyclohexanone oxime synthesis zone and that an organic medium comprising the organic solvent and cyclohexanone oxime is withdrawn from the cyclohexanone oxime synthesis zone.

10. Process according to claim 9 characterized that the aqueous reaction medium and a stream comprising the cyclohexanone and the organic solvent are contacted in countercurrent flow.

11. Process according to claim 9 or claim 10, characterized in that the cyclohexanone oxime concentration in the organic medium exiting the cyclohexanone oxime synthesis zone is higher than 5 wt. %.

12. Process according to claim 11, characterized in that the cyclohexanone oxime concentration in the organic medium exiting the cyclohexanone oxime synthesis zone is higher than 25 wt. %.

* * * * *